United States Patent [19]

Eloy et al.

[11] B 3,992,539

[45] Nov. 16, 1976

[54] S-TRIAZOLO-[3,4-A]ISOQUINOLINES IN TREATING INFLAMMATORY DISORDERS

[75] Inventors: Fernand G. F. Eloy, Rhode St. Genese, Belgium; Robert W. Shanahan, Allendale, N.J.

[73] Assignee: Mallinckrodt Chemical Works, St. Louis, Mo.

[22] Filed: Dec. 12, 1973

[21] Appl. No.: 426,639

[44] Published under the second Trial Voluntary Protest Program on February 3, 1976 as document No. B 426,639.

Related U.S. Application Data

[62] Division of Ser. No. 164,880, July 26, 1971, abandoned.

[52] U.S. Cl. .............................. 424/258; 424/248; 424/250

[51] Int. Cl.$^2$ ............... A61K 31/47; A61K 31/495; A61K 31/535

[58] Field of Search ................... 260/288; 424/258

[56] References Cited

UNITED STATES PATENTS

| 2,719,158 | 9/1955 | Druey et al. .................. 260/288 R |
|---|---|---|
| 3,354,164 | 11/1967 | Francis ............................ 260/288 |
| 3,663,551 | 5/1972 | Deryckere et al. ........... 260/283 SY |

FOREIGN PATENTS OR APPLICATIONS

1,573,135  7/1969  France .............................. 260/288

*Primary Examiner*—Stanley J. Friedman
*Attorney, Agent, or Firm*—Koenig, Senniger, Powers and Leavitt

[57] ABSTRACT

Novel s-triazolo-[3,4-a]-isoquinoline compounds are prepared by methods analogous to known methods and exhibit anti-inflammatory activity.

5 Claims, No Drawings

S-TRIAZOLO-[3,4-A]ISOQUINOLINES IN TREATING INFLAMMATORY DISORDERS

This is a division of application Ser. No. 164,880, filed July 26, 1971, now abandoned.

BACKGROUND OF THE INVENTION

The present invention relates to the pharmaceutical field, and more particularly to methods and pharmaceutical compositions for treating mammals utilizing as active agents certain novel organic heterocyclic compounds from the class known as s-triazolo-[3,4-a]-isoquinolines.

The preparation of various s-triazolo-[3,4-a]-isoquinolines is disclosed by (1) S. Naqui et al., *Indian J. Chem.*, 3, 162–4 (1965); (2) G. S. Sidhu et al., *Jour. Heterocyclic Chem.*, 3, 158–164 (1966); (3) J. E. Francis, U.S. Pat. No. 3,354,164 (1967); (4) H. K. Reimlinger et al., French Pat. No. 1,573,135 (1969) and (5) H. K. Reimlinger et al., *Chem. Ber.* 103, 1960–1981 (1970).

No pharmaceutical compositions or utility are disclosed in references (1), (2), (4) and (5) cited above. Francis (3) discloses that unsubstituted s-triazolo-[3,4-a]-isoquinoline and its 3-lower alkyl derivatives are coronary vasodilators.

The invention is particularly concerned with certain novel compounds useful in the treatment of inflammatory disorders, among which are the conditions known as arthritis.

The term "arthritis" is applied to a group of related disorders of the joints which are characterized by pain, inflammation and stiffness. Certain types of arthritis are due to specific infectious agents, but no specific cause is known for the most common type, known as rheumatoid arthritis. While this is primarily an inflammatory disease of the joints, it is sometimes accompanied by pedal edema, that is, an accumulation of fluid in the tissues of the foot. Treatment of this disease involves the administration of agents which have been found effective in reducing the pain and the inflammation. Such agents have come to be generally known as anti-inflammatory agents.

Chemical compounds having structures of varying complexity, from the structurally simple aspirin to relatively complex steroid compounds, are known to be useful anti-inflammatory agents in the treatment of arthritic and related disorders in man and other mammals. Among such recognized anti-inflammatory agents, in addition to aspirin, are the following, to which reference may be conveniently made in the Merck Index, 8th Ed., Merck & Co., Rahway, N.J. (1968): dexamethasone (p. 334), hydrocortisone (p. 542) indomethacin (p. 566), mefenamic acid (p. 648) and phenylbutazone (p. 815). However, s-triazolo-[3,4-a]-isoquinoline compounds have not heretofore been recognized as having anti-inflammatory activity.

SUMMARY OF THE INVENTION

Among the several objects of the invention may be noted the provision of certain novel s-triazolo-[3,4-a]-isoquinolines; the provision of such compounds which exhibit anti-inflammatory activity; and the provision of pharmaceutical compositions and methods for combatting an inflammatory reaction in a susceptible mammal, which compositions and methods utilize the novel s-triazolo-[3,4-a]-isoquinolines as active agents. Other objects will be in part apparent and in part pointed out hereinafter.

The present invention is thus directed to novel s-triazolo-[3,4-a]-isoquinoline compounds from the group hereinafter specifically set forth. The invention is also directed to a method of combatting an inflammatory reaction in a susceptible mammal by administering to said mammal an effective amount of such an s-triazolo-[3,4-a]-isoquinoline compound and to pharmaceutical compositions comprising such a compound and a pharmaceutical carrier.

DESCRIPTION OF THE PREFERRED EMBODIMENTS

In accordance with the present invention, it has now been found that certain novel s-triazolo-[3,4-a]-isoquinoline compounds exhibit activity as anti-inflammatory agents. The type and degree of activity observed with s-triazolo-[3,4-a]-isoquinoline compounds is selective in nature and the presence or absence of such activity, and its degree when present, appears to be quite sensitive to the position and type of substitution on the basic s-triazolo-[3,4-a]-isoquinoline structure.

The novel s-triazolo-[3,4-a]-isoquinoline compounds of the invention which have been found to possess anti-inflammatory activity are:

3-(N,N-diethylaminoethylamino)-s-triazolo-[3,4-a]-isoquinoline
3-trifluoromethyl-6-carbomethoxy-s-triazolo-[3,4-a]-isoquinoline
3-(N-methylpiperazino)-6-chloro-s-triazolo-[3,4-a]-isoquinoline
3-isobutyl-s-triazolo-[3,4-a]-isoquinoline
8,9-methylenedioxy-s-triazolo-[3,4-a]-isoquinoline
3-trifluoromethyl-6-methyl-s-triazolo-[3,4-a]-isoquinoline
3-trifluoromethyl-8,9-methylenedioxy-s-triazolo-[3,4-a]-isoquinoline
3-trifluoromethyl-9-methoxy-s-triazolo-[3,4-a]-isoquinoline
3-methyl-9-methoxy-s-triazolo-[3,4-a]-isoquinoline
3-methyl-8-methoxy-s-triazolo-[3,4-a]-isoquinoline
3-trifluoromethyl-9-chloro-s-triazolo-[3,4-a]-isoquinoline
3-trifluoromethyl-8-methoxy-s-triazolo-[3,4-a]-isoquinoline
3-trifluoromethyl-6-carboxy-s-triazolo-[3,4-a]-isoquinoline
3-trifluoromethyl-9-methyl-s-triazolo-[3,4-a]-isoquinoline
3-methyl-7-cyano-s-triazolo-[3,4-a]-isoquinoline
3-acetoxymethyl-s-triazolo-[3,4-a]-isoquinoline
3-n-propyl-7-bromo-s-triazolo-[3,4-a]-isoquinoline
3-methyl-7-chloro-s-triazolo-[3,4-a]-isoquinoline
3-morpholinomethyl-7-chloro-s-triazolo-[3,4-a]-isoquinoline
3-trifluoromethyl-5,6-dihydro-9-methoxy-s-triazolo-[3,4-a]-isoquinoline
5,6-dihydro-8,9-methylenedioxy-s-triazolo-[3,4-a]-isoquinoline and the pharmaceutically acceptable, nontoxic acid additions salts thereof. Such addition salts may be derived from hydrochloric acid, hydrobromic acid, phosphoric acid, methanesulfonic acid and the like. Also useful are the alkali metal salts of 3-trifluoromethyl6-carboxy-s-triazolo-[3,4-a]-isoquinoline, such as potassium 6-carboxylate-3-trifluoromethyl-s-triazolo-[3,4-a]-isoquinoline, for example.

In addition to anti-inflammatory activity, certain of the compounds (e.g., 3-(N,N-diethylaminoethylamine)-s-triazolo-[3,4-a]-isoquinoline, 3-trifluoromethyl9-methyl-s-triazolo-[3,4-a]-isoquinoline, 8,9-methylenedioxy-s-triazolo-[3,4-a]-isoquinoline, 3-isobutyl-striazolo-[3,4-a]-isoquinoline and 3-trifluoromethyl-6-carbomethoxy-s-triazolo-[3,4-a]-isoquinoline) advantageously exhibit anti-secretory activity rather than the ulcerogenic properties exhibited by certain prior art anti-inflammatory agents, such as the cortical steroids.

In general, the novel s-triazolo-[3,4-a]-isoquinoline compounds of the invention may be prepared by the reaction of 1-hydrozinoisoquinoline with an acidic reagent as disclosed in H. K. Reimlinger et al. French Patent 1,573,135 (1969), either in the presence or absence of a solvent. As illustrated by the working examples hereinafter, many of the s-triazolo-[3,4-a]-isoquinolines of the invention may be prepared directly from the corresponding ring-substituted hydrazinoisoquinoline and the specific acidic agent. In other instances (e.g., 3-(N,N-diethylaminoethylamino)-s-triazolo-[3,4-a]-isoquinoline and 3-methyl-7-cyano-s-triazolo-[3,4-a]-isoquinoline), substitution is carried out after ring closure. In the case of the 5,6-dihydro-s-triazolo[3,4-a]-isoquinoline compounds of the inventioin, both 3-trifluoromethyl-5,6-dihydro-9-methoxy-s-triazolo-[3,4-a]-isoquinoline and 5,6-dihydro-8,9-methylenedioxy-s-triazolo-[3,4-a]-isoquinoline may be prepared by electrolytic or catalytic hydrogenation.

In further accordance with the invention, pharmaceutical compositions and methods useful for combatting inflammatory reactions in susceptible mammals are provided, the compositions comprising an aforementioned s-triazolo-[3,4-a]-isoquinoline compound and a pharmaceutical carrier which may be either liquid or solid material. These compositions may be administered orally or parenterally in the usual pharmaceutical forms including capsules, tablets, solutions, suspensions and the like. For example, the s-triazolo-[3,4-a]-isoquinoline compounds may be formulated with carriers such as magnesium stearate and lactose and filled into gelatin capsules. Examples of other solid pharmaceutical carriers, such as fillers, binders and lubricants, include dibasic calcium phosphate, calcium sulfate dihydrate, microcrystalline cellulose, calcium carbonate and talc. The pharmaceutical compositions of the invention may also be in the form of sterile parenteral solutions with the s-triazolo-[3,4-a]-isoquinoline compound dissolved in a sterile parenteral solvent such as polyethylene glycol, propylene glycol, water or mixtures of solvents or the compositions may be in the form of suspensions.

Where the s-triazolo-[3,4-a]-isoquinoline compound is water-insoluble, it is preferred that the compound be formulated into the pharmaceutical compositions of the invention in a micronized form, as by milling the compound by conventional methods. More particularly, it is preferred that the compound be micronized to a particle size of approximately 1–10 microns.

The following examples illustrate the invention.

In each of Examples 1–22, the indicated structure was confirmed by infrared spectroscopy.

EXAMPLE 1

Preparation of 3-isobutyl-s-triazolo-[3,4-a]-isoquinoline:

A. Preparation of 1-isovalerylhydrazinoisoquinoline:

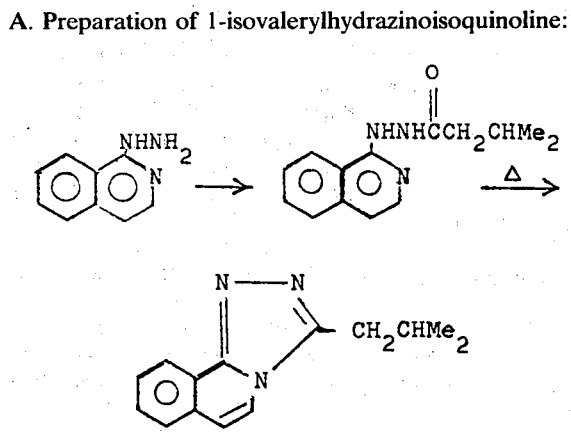

A mixture of 1-hydrazinoisoquinoline (15.8 g., 0.1 mol.) and dicyclohexylcarbodimide (20.6 g., 0.1 mol.) in methylene chloride (600 ml.) was stirred and cooled in an ice bath and isovaleric acid (10.2 g., 0.1 mol.) was added dropwise. After stirring for three hours, the dicyclohexylurea was removed by filtration and the solvent was evaporated at ca. 40°C. The residue was recrystallized from benzene to provide 15.4 g. (64%) of the acid hydrazide, m.p. 170°C.

B. Thermolysis of the Acid Hydrazide:

The acid hydrazide (7.26 g., 0.03 mol.) was allowed to reflux in o-dichlorobenzene (100 ml.) for one hour and slowly allowed to cool to room temperature.

The solvent was removed in vacuo and the residue was recrystallized (after treatment with decolorizing carbon) from benzene to provide the product, 1.0 g. (14%) as fine, while crystals, m.p. 153°–154°C.

Calculated for $C_{14}H_{15}N_3$: C, 74.68; H, 6.66; N, 18.65. Found: C, 74.49; H, 6174; N, 18.94.

EXAMPLE 2

Preparation of 3-Trifluoromethyl-6-methyl-s-triazolo-[3,4-a]-isoquinoline:

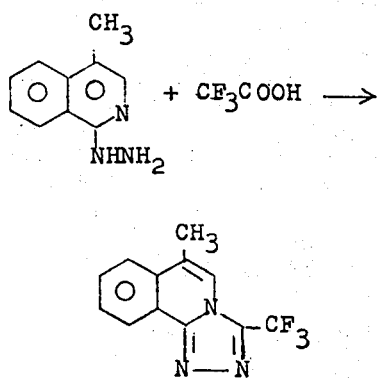

1-Hydrazino-4-methylisoquinoline (5.0 g.) and trifluoroacetic acid (70 ml.) were heated at reflux for three hours. After removal of the excess trifluoroacetic acid, the residue was dissolved in chloroform and extracted with sodium carbonate solution. The organic layer was dried and concentrated and the residue was recrystallized from a cyclohexane-benzene (70/30) mixture to provide the product in a yield of 65%, m.p. 162°–164°C.

Calculated for $C_{11}H_8F_3N_3$: C, 57.40; H, 3.18; N, 16.75. Found: C, 57.88; H, 3.08; N, 16.74.

EXAMPLE 3

Preparation of 3-Trifluoromethyl-6-carbomethoxy-s-triazolo-[3,4-a]-isoquinoline:

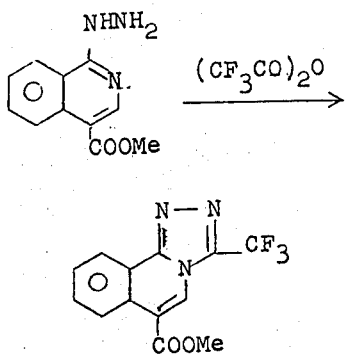

Excess trifluoroacetic anhydride and 1-hydrazino-4-methoxycarbonylisoquinoline were allowed to reflux for one hour and the excess anhydride was removed under reduced pressure. The residue was recrystallized from a mixture of benzene and cyclohexane to provide the product, m.p. 170°C.

Calculated for $C_{13}H_8F_3N_3O_2$: C, 52.90; H, 2.71; N, 14.25. Found: C, 52.84; H, 2.92; N, 13.71.

EXAMPLE 4

Preparation of 3-Trifluoromethyl-6-carboxy-s-triazolo-[3,4-a]-isoquinoline, Potassium Salt:

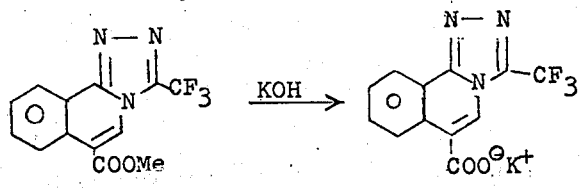

A solution of 3-trifluoromethyl-6-methoxycarbonyl-s-triazolo-[3,4-a]-isoquinoline (7.4 g., 0.025 mol.) and potassium hydroxide (1.4 g., 0.025 mol.) in 140 ml. of ethanol was heated at reflux for 12 hours. The solvent was removed under reduced pressure and the residue was partially dissolved in water. After filtration, the aqueous solution was concentrated under reduced pressure to give a residue which was dissolved in ethanol and treated with decolorizing carbon. Addition of ether to the ethanolic solution provided a light pink solid as the product, 4.9 g. (62%).

EXAMPLE 5

Preparation of 3-Trifluoromethyl-6-carboxy-s-triazolo-[3,4-a]-isoquinoline:

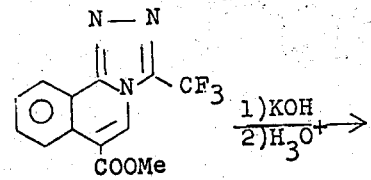

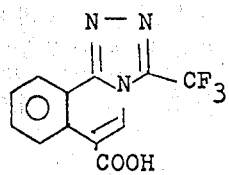

A solution of potassium hydroxide (2.8 g., 0.05 mol.) and 3-trifluoromethyl-6-methoxycarbonyl-s-triazolo-[3,4-a]-isoquinoline (14.8 g., 0.05 mol.) was allowed to reflux in 280 ml. of ethanol for 12 hours. Removal of the solvent provided a residue which was dissolved in water and filtered. The aqueous filtrate was neutralized with 2N hydrochloric acid and the product, 9.7 g. (70%) was collected by filtration; m.p. 290°C. (dec.).

Calculated for $C_{12}H_6F_3N_3O_2$: C, 51.22; H, 2.13; N, 14.94. Found: C, 51.58; H, 1.92; N, 14.83.

EXAMPLE 6

Preparation of 3-Methyl-8-methoxy-s-triazolo-[3,4-a]-isoquinoline:

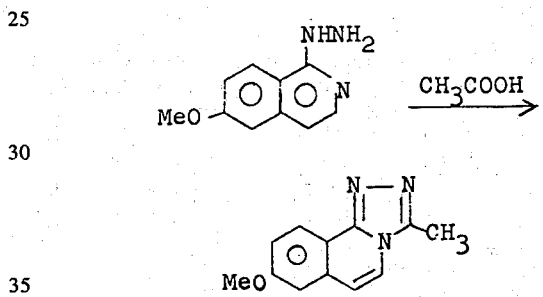

1-Hydrazino-6-methoxyisoquinoline (9.6 g., 0.05 mol.) was dissolved in glacial acetic acid (190 ml.) and the solution was heated at reflux for four hours. Excess acetic acid was removed in vacuo to provide a brown oil. The oil was slurried in water and was treated with potassium bicarbonate to yield a solid. The solid was treated with decolorizing carbon and was recrystallized three times from benzene to give the product in a yield of 24%; m.p. 183°–184°C.

Calculated for $C_{12}H_{11}N_3O$: C, 67.60; H, 5.16; N, 19.71; O, 7.50. Found: C, 67.60; H, 5.02; N, 19.68; O, 7.70.

EXAMPLE 7

Preparation of 3-Trifluoromethyl-8-methoxy-s-triazolo-[3,4-a]-isoquinoline:

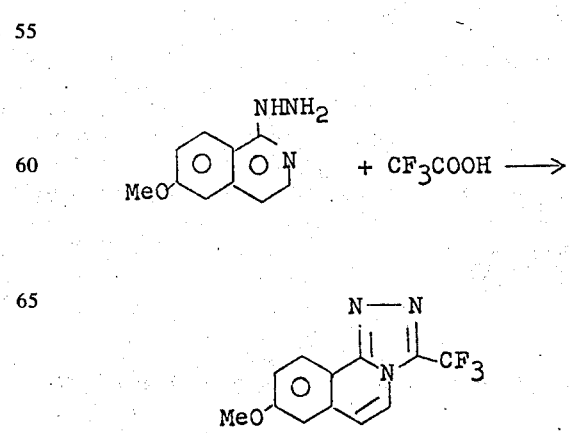

A solution of 1-hydrazino-6-methoxyisoquinoline and excess trifluoroacetic acid was held at reflux for four hours. After removal of the excess acid, the residue was treated with potassium bicarbonate solution until neutral and filtered. The filter cake was recrystallized from ethanol to provide the product in a yield of 20%; m.p. 214°–215°C.

Calculated for $C_{13}H_8F_3N_3O$: C, 53.95; H, 2.99; N, 15.72. Found: C, 54.63; H, 3.17; N, 15.49.

EXAMPLE 8

Preparation of 3-Methyl-9-methoxy-s-triazole-[3,4-a]-isoquinoline:

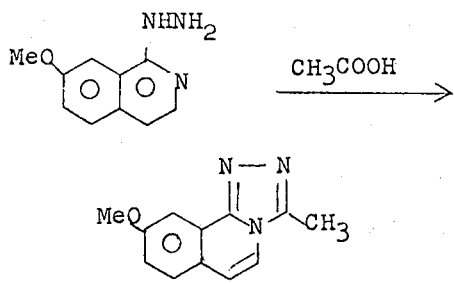

1-Hydrazino-7-methoxyisoquinoline was allowed to reflux for three hours with excess glacial acetic acid. After removal of the excess acid, the solid was dissolved in chloroform and washed with sodium carbonate solution. The organic layer was dried and was concentrated in vacuo to provide the crude product. Recrystallization from benzene gave the pure product in a yield of 68%; m.p. 156°–158°C.

Calculated for $C_{12}H_{11}N_3O$: C, 67.60; H, 5.16; N, 19.70. Found: C, 67.48; H, 5.19; N, 19.82.

EXAMPLE 9

Preparation of 3-Trifluoromethyl-9-chloro-s-triazolo-[3,4-a]-isoquinoline:

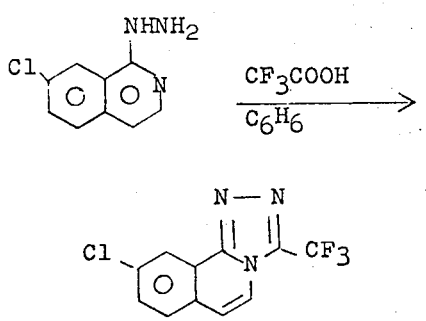

A solution of the 7-chloro-1-hydrazinoisoquinoline (7.5 g., 0.038 mol.) and trifluoroacetic acid (20 ml.) in benzene was allowed to reflux for three hours. After concentration in vacuo, the gummy crystals were dissolved in chloroform and washed with sodium carbonate. Removal of the solvent in vacuo provided 9.8 g. of a brown solid, m.p. 228°C. Successive recrystallization from ethanol provided the product, 3.7 g. (32%); m.p. 238°–239°C.

EXAMPLE 10

Preparation of 8,9-Methylenedioxy-s-triazolo-[3,4-a]-isoquinoline:

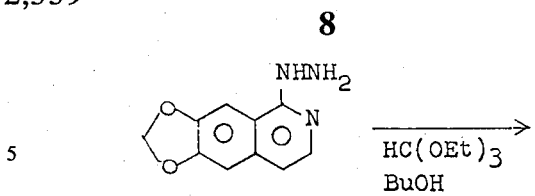

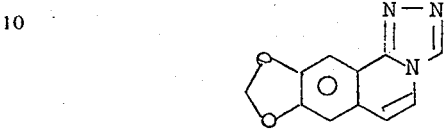

1-Hydrazino-6,7-methylenedioxylisoquinoline (25 g.) and 10 ml. of ethyl orthoformate were allowed to reflux for five hours in 70 ml. of 1-butanol. Evaporation of the solvent in vacuo and recrystallization from toluene provided the product in a yield of 71%; m.p. 267°–269°C.

Calculated for $C_{11}H_6N_3O_2$: C, 62.00; H, 3.28; N, 19.70. Found: C, 61.32; H, 3.37; N, 19.48.

EXAMPLE 11

Preparation of 3-Trifluoromethyl-8,9-methylenedioxy-s-triazolo-[3,4-a]-isoquinoline:

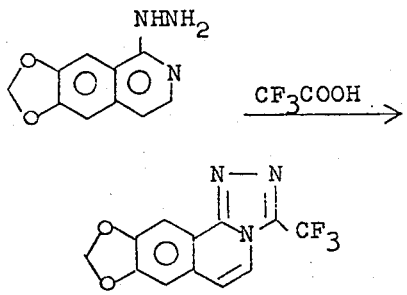

1-Hydrazino-6,7-methylenedioxyisoquinoline was heated at reflux with excess trifluoroacetic acid. Concentration of the solution in vacuo, provided a residue which was slurried with sodium carbonate solution and filtered. The filter cake was recrystallized from ethanol to yield the product in a yield of 60%; m.p. 187°–189°C.

Calculated for $C_{12}H_4F_3N_3O_2$: C, 51.20; H, 2,35; N, 14.95. Found: C, 51.11; H, 2.16; N, 14.91.

EXAMPLE 12

Preparation of 3-(N-methylpiperazino)-6-chloro-s-triazolo-[3,4-a]-isoquinoline:

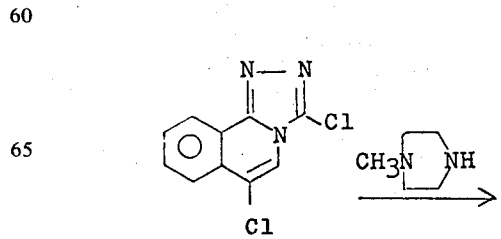

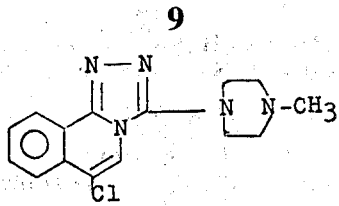

N-methylpiperazine (5 g., 0.05 mol.) and 3,6-dichloro-s-triazoli-[3,4-a]-isoquinoline (3 g., 0.025 mol.) were heated at 160°C. for four hours. On cooling, a solid formed which was dissolved in water. The addition of an aqueous solution of potassium carbonate precipitated the impure product as an oil which was repeatedly recrystallized from ethanol and washed with ether to provide the pure product in a yield of 82%, m.p. 150°–153°C.

Calculated for $C_{15}H_{16}N_5Cl$: C, 59.70; H, 5.31; N, 23.20. Found: C, 59.39; N, 5.28; N, 23.25.

EXAMPLE 13

Preparation of 3-(N,N-diethylaminoethylamino)-s-triazolo-[3,4-a]-isoquinoline:

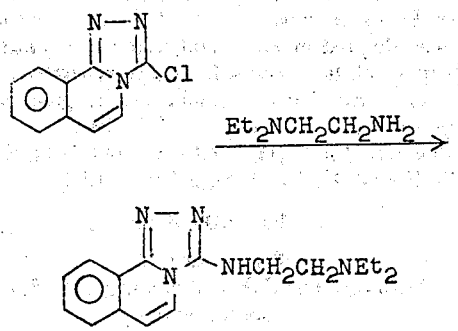

3-Chloro-s-triazolo-[3,4-a]-isoquinoline (5.1 g., 0.025 mol.) was heated at reflux for three hours in diethylaminoethylamine (28 ml.). The excess amine was removed by distillation under reduced pressure to provide a crystalline solid. The solid as dissolved in water, treated with aqueous sodium carbonate and was extracted with dichloromethane. After drying and concentration of the organic extract, the residue was repeatedly recrystallized from toluene and washed with a small amount of ether to provide the product, 3.8 g. (54%); m.p. 163°C.

Calculated for $C_{16}H_{21}N_5$: C, 67.84; H, 7.42; N, 24.73. Found: C, 67.67; H, 7.60; N, 24.63.

EXAMPLE 14

Preparation of Intermediate for 3-methyl-7-cyano-s-triazolo-[3,4-a]-isoquinoline:

3-Methyl-7-bromo-s-triazolo-[3,4-a]-isoquinoline was prepared from acetyl chloride and 5-bromo-1-hydrazinoisoquinoline by a method generally similar to that described below for the preparation of 3-methyl-7-chloro-s-triazolo-[3,4-a]-isoquinoline. Yield, 78.5%; m.p. 203°–204°C.

Calculated for $C_{11}H_8N_3Br$: C, 50.40%; H, 3.08%; N, 16.03%; Br, 30.49% Found: C, 50.28%; H, 3.28%; N, 15.99%; Br, 30.25%

Preparation of 3-Methyl-7-cyano-s-triazolo-[3,4-a]-isoquinoline:

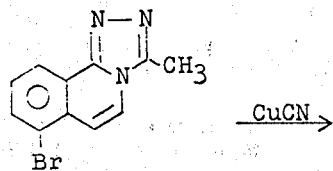

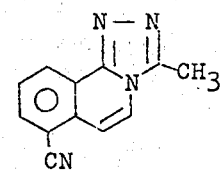

3-Methyl-7-bromo-s-triazolo-[3,4-a]-isoquinoline (7.9 g., 0.03 mol.) and cuprous cyanide (4.5 g., 0.05 mol.) were heated in 25 ml. of quinoline at 180°C. for 1.25 hr. After cooling to room temperature, the reaction mixture was extracted with dichloromethane and chloroform.

The residue was treated with a mixture of chloroform and aqueous sodium cyanide (15 g.) and filtered to remove ca. 1.3 g. of crude product, m.p. 285°–289°C. The chloroform extracts were concentrated in vacuo and the residue was partially dissolved in hot acetonitrile and filtered to provide an additional 2.5 g. of crude product, m.p. 280°–285°C. The acetonitrile solution contained 1.2 g. of starting material.

The crude product 2.5 g., was suspended in 15 ml. of ethanol and treated with 0.9 ml. of hydrobromic acid. After stirring this suspension for two hours, the suspension was filtered and the filter cake washed with ethanol-ether and dried to provide the product, m.p. 285°–289°C.

Calculated for $C_{12}H_8N_4$: C, 69.22; H, 3.87; N, 26.91. Found: C, 68.33 (+0.6% ash); H, 4.03; N, 26.65.

EXAMPLE 5

Preparation of 3-Propyl-7-bromo-s-triazolo-[3,4-a]-isoquinoline:

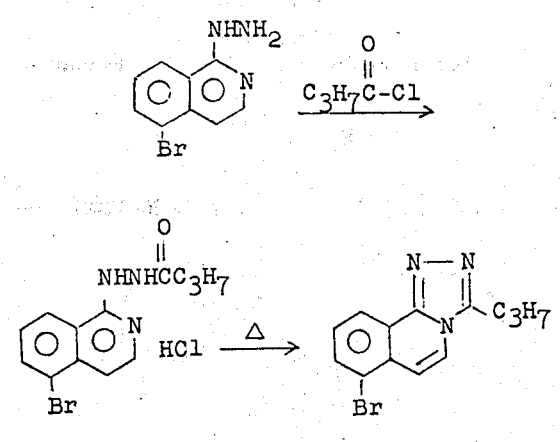

A mixture of 5-bromo-1-hydrazinoisoquinoline (4.76 g., 0.02 mol.) and butyryl chloride (2.1 ml., 0.02 mol.) in dichloromethane (100 ml.) was allowed to reflux overnight. The solvent was removed in vacuo and the residue was heated at reflux for three hours in xylene (100 ml.) and triethylamine (2.8 ml., 0.02 mol.). The mixture was filtered and the xylene removed in vacuo to provide the crude product. Recrystallization from ethanol (≈100 ml.) gave the pure product, 4.4 g. (76%); m.p. 197°–199°C., m.p. (hydrochloride salt) 200°–201°C.

Calculated for $C_{13}H_{12}BrN_3$: C, 53.81; H, 4.17; N, 14.48; Br, 27.54. Found: C, 54.09; H, 4.26; N, 14.32; Br, 27.80.

EXAMPLE 16

Preparation of 3-Methyl-7-chloro-s-triazolo-[3,4-a]-isoquinoline:

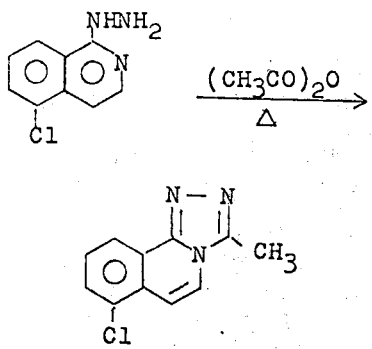

Acetic anhydride (20 ml.) and 5-chloro-1-hydrazinoisoquinoline (2.5 g.) were heated at reflux for one hour and the mixture was concentrated under reduced pressure. After washing with water and drying, 2.5 g. of crude product was obtained. This material was recrystallized from benzene (70 ml.) to provide the pure product in a yield of 51%; m.p. 191°–191.5°C., m.p. (hydrochloride salt) 228°–232°C.

Calculated for $C_{11}H_8N_3Cl$: C, 60.70; H, 3.71; N, 19.31; Cl, 16.29. Found: C, 60.43; H, 3.77; N, 19.45; Cl, 16.30.

Calculated for $C_{11}H_8N_3Cl \cdot HCl$: C, 51.99; H, 3.57; N, 16.54; Cl, 27.90. Found: C, 51.56; H, 3.71; N, 16.24; Cl, 27.52.

EXAMPLE 17

Preparation of 3-Acetoxymethyl-s-triazolo-[3,4-a]-isoquinoline:

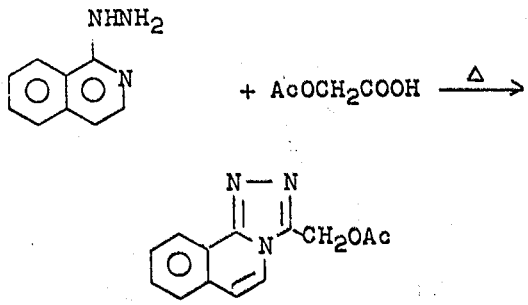

1-Hydrazinoisoquinoline was heated with excess acetoxyglycolic acid. The residue was cooled, dissolved in chloroform and washed with sodium carbonate solution. The chloroform extracts were dried and concentrated in vacuo to provide the crude product which was purified by recrystallization from benzene.

Calculated for $C_{13}H_{11}N_3O_2$: C, 64.8; H, 4.57; N, 17.50. Found: C, 64.85; H, 4.58; N, 17.39.

EXAMPLE 18

Preparation of 3-Trifluoromethyl-9-methoxy-s-triazolo-[3,4-a]-isoquinoline:

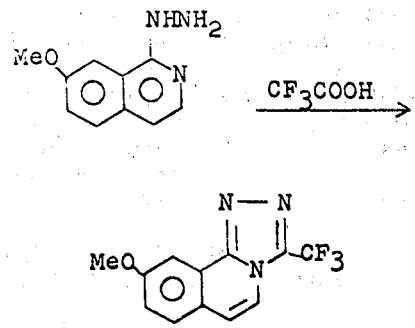

A solution of 1-hydrazino-7-methoxyisoquinoline in excess trifluoroacetic acid was allowed to reflux for 2 hours. Excess acid was removed in vacuo and the residue was slurried in water and treated with sodium bicarbonate solution. The solid was removed by filtration and recrystallized from cyclohexane to give the product in a yield of 70%; m.p. 152°–154°C.

Calculated for $C_{12}H_8F_3N_3O$: C, 54.00; H, 3.00; N, 15.75. Found: C, 54.01; H, 3.16; N, 15.77.

EXAMPLE 19

Preparation of 3-Trifluoromethyl-9-methyl-s-triazolo-[3,4-a]-isoquinoline:

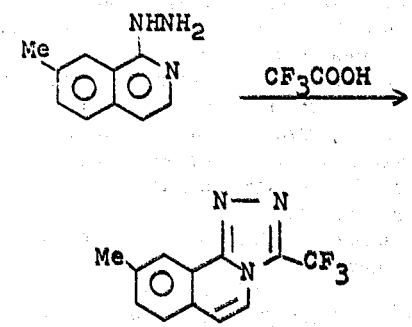

A solution of 1-hydrazino-7-methylisoquinoline in excess trifluoroacetic acid was allowed to reflux for two hours. Removal of the excess acid in vacuo, treatment of the residue with sodium bicarbonate solution and filtration provided the crude product which was recrystallized from cyclohexane to give the product in a yield of 20%; m.p. 205°–206°C.

Calculated for $C_{12}H_8F_3N_3$: C, 57.40; H, 3.18; N, 16.72. Found: C, 57.28; H, 3.33; N, 16.40.

EXAMPLE 20

Preparation of 3-Trifluoromethyl-5,6-dihydro-9-methoxy-s-triazolo-[3,4-a]-isoquinoline Hydrochloride:

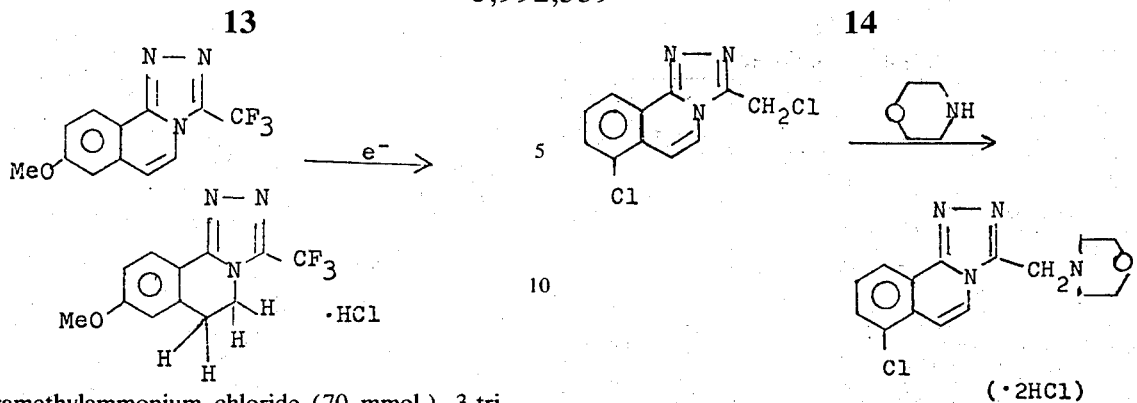

Tetramethylammonium chloride (70 mmol.), 3-trifluoromethyl-9-methoxy-s-triazolo-[3,4-a]-isoquinoline (14 mmol.) and methanol (70 ml.) were placed at the cathode of an electrochemical cell and water (2 ml.), methanol (20 ml.) and allyl alcohol (3 ml.) were placed at the anode. Reduction was carried out at a constant voltage of 5 volts and the current varied from 0.1 to 0.42 amperes. On completion of the reduction, the methanolic layer was concentrated and water was added and the solution was extracted with benzene and ether. The organic layers were combined and concentrated and the residue was treated with conc. hydrochloric acid. After evaporation, the solid residue was recrystallized from ethanol to yield the product in a yield of 70%.

Calculated for $C_{12}H_{10}F_3N_3O$ . HCl: N, 13.75. Found: N, 13.60.

EXAMPLE 21

Preparation of 5,6-Dihydro-8,9-methylenedioxy-s-triazolo-[3,4-a]-isoquinoline, Hydrochloride:

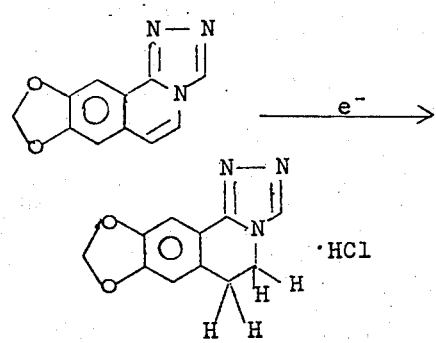

In an electrochemical cell, 8,9-methylenedioxy-s-triazolo-[3,4-a]-isoquinoline (20 mmol.), tetramethylammonium chloride (100 mmol.) and methanol (70 ml.) in the cathode and at the anode were placed water (2 ml.), allyl alcohol (3 ml.) and methanol (30 ml.). Electrolysis was carried out at a voltage of 5 volts and the current varied from 0.08 to 0.48 amperes. On completion of the reduction, the methanolic solution was concentrated; the concentrate was suspended in water, and the aqueous solution was extracted repeatedly with ethyl acetate. Concentration of organic extracts, treatment of the crystalline residue with conc. hydrochloric acid, evaporation, and recrystallization from ethanol gave the product in a yield of 33.8%; m.p. 220°–227°C.

Calculated for $C_{11}H_9N_3O_2$ . HCl: C, 52.63; H, 4.01; N, 16.70. Found: C, 52.56; H, 4.25; N, 16.12

EXAMPLE 22

Preparation of 7-Chloro-3-morpholinomethyl-s-triazolo-[3,4-a]-isoquinoline (Dihydrochloride):

A solution of 7-chloro-3-chloromethyl-s-triazolo-[3,4-a]-isoquinoline (3.2 g., 12.6 mmol.) in 75 ml. of toluene was stirred at reflux with 8.7 ml. of morpholine (0.1 mol.) for 2 hr. The solvent was removed in vacuo and the residue was washed with water and filtered to give the product, as a crystalline solid, 2.77 g. (72%); m.p. 180°–182°C. The dihydrochloride salt was prepared from methanolic hydrogen chloride; m.p. 230°–234°C.

Calculated for $C_{15}H_{15}ClN_4O$: C, 59.50; H, 4.99; N, 18.50. Found: C, 59.22; H, 5.14; N, 18.47.

Calculated for $C_{15}H_{15}ClN_4O$ . 2 HCl: C, 47.95; H, 4.56; N, 14.95; O, 4.26. Found: C, 47.49; H, 4.89; N, 14.76; O, 4.95.

EXAMPLE 23

The anti-inflammatory activity of a number of representative compounds of the invention was determined by measuring inhibition of carrageenin-induced pedal edema in rats. The procedure used was a modification of the method of Winter et al., Proc. Soc. Exptl. Biol. Med. 111:544 (1962). The device used for measurement of the paw volume was an adaptation of the water displacement procedure described by Adamkiewicz et al., Can. J. Biochem. Physiol. 33: 332 (1955). The compounds were studied for their effectiveness in inhibiting the edema caused by the intraplantar injection of 0.05 ml. of a sterile 1.0% solution of carrageenin. Rats (male Wistar, 100 to 175 grams) were employed and were fasted for approximately 18 hours prior to use.

Each compound was administered as a finely divided suspension in a 0.25% methylcellulose solution. The compounds were administered orally one hour prior to the injection of the phlogistic substance (carrageenin) into the left hind paw of the rats. At peak swelling time (3 hours), the volume of edema was calculated by differential paw volumes. The $ED_{50}$ value was obtained for each compound and is defined as that dose which reduced edema formation by 25% or more compared with the mean control response (parallel run) in 50% of the animals. The results were as follows:

Table 1

| Compound | Anti-Inflammatory Activity ($ED_{50}$ - mg./kg.) |
|---|---|
| 3-(N,N-diethylaminoethylamino)-s-triazolo-[3,4-a]-isoquinoline | 172 |
| 3-isobutyl-s-triazolo-[3,4-a]-isoquinoline | 130 |
| 8,9-methylenedioxy-s-triazolo-[3,4-a]-isoquinoline | approx. 24 |
| 3-trifluoromethyl-8,9-methylene- | |

Table 1-continued

| Compound | Anti-Inflammatory Activity (ED$_{50}$ - mg./kg.) |
|---|---|
| dioxy-s-triazolo-[3,4-a]-isoquinoline | 80 |
| 3-trifluoromethyl-9-methoxy-s-triazolo-[3,4-a]-isoquinoline | 39 |
| 3-methyl-9-methoxy-s-triazolo-[3,4-a]-isoquinoline | 115 |
| 3-methyl-8-methoxy-s-triazolo-[3,4-a]-isoquinoline | 135 |
| 3-trifluoromethyl-9-chloro-s-triazolo-[3,4-a]-isoquinoline | approx. 160 |
| 3-trifluoromethyl-9-methyl-s-triazolo-[3,4-a]-isoquinoline | approx. 160 |
| 3-methyl-7-cyano-s-triazolo-[3,4-a]-isoquinoline hydrobromide | <100 |
| 3-acetoxymethyl-s-triazolo-[3,4-a]-isoquinoline | approx. 100 |
| 3-morpholinomethyl-7-chloro-s-triazolo-[3,4-a]-isoquinoline dihydrochloride | approx. 160 |
| 3-trifluoromethyl-5,6-dihydro-9-methoxy-s-triazolo-[3,4-a]-isoquinoline hydrochloride | 38 |
| 5,6-dihydro-8,9-methylenedioxy-s-triazolo-[3,4-a]-isoquinoline hydrochloride | approx. 160 |
| 3-(N-methylpiperazino)-6-chloro-s-triazolo-[3,4-a]-isoquinoline | >60 |
| 3-trifluoromethyl-6-carboxy-s-triazolo-[3,4-a]-isoquinoline, potassium salt | >160 |
| 3-methyl-7-chloro-s-triazolo-[3,4-a]-isoquinoline hydrochloride | >30 |

Typical ED$_{50}$ values from the same test for known anti-inflammatory agents are as follows:

Table 2

| Drug | Anti-Inflammatory Activity (ED$_{50}$ - mg./kg.) |
|---|---|
| Aspirin | 224 |
| Phenylbutazone | 30 |
| Hydrocortisone Acetate | 26 |
| Indomethacin | 2.4 |
| Dexamethasone | 0.18 |

EXAMPLE 24

The anti-secretory properties of certain compounds of the invention was determined using the following procedure. The stomachs of fasting rats were ligated at the pylorus (Shay rat procedure) immediately followed by an intraperitoneal injection of 50 mg./kg. of each compound tested. Four hours later the animals were sacrificed, the stomachs removed and the total volume of fluid was measured.

The results were as follows:

Table 3

| Compound | Anti-Secretory Activity (% Reduction)* |
|---|---|
| 3-(N,N-diethylaminoethylamino)-s-triazolo-[3,4-a]-isoquinoline | 49% |
| 3-trifluoromethyl-6-carbomethoxy-s-triazolo-[3,4-a]-isoquinoline | 6.4 |
| 3-isobutyl-s-triazolo-[3,4-a]-isoquinoline | 16 |
| 8,9-methylenedioxy-s-triazolo-[3,4-a]-isoquinoline | 29.5 |
| 3-trifluoromethyl-9-methyl-s-triazolo-[3,4-a]-isoquinoline | 22 |

*% Reduction of gastric secretion (ml./100 gm.) after subcutaneous administration to fasting rats at 50 mg./kg.

In view of the above, it will be seen that the several objects of the invention are achieved and other advantageous results attained.

As various changes could be made in the above methods and compositions without departing from the scope of the invention, it is intended that all matter contained in the above description shall be interpreted as illustrative and not in a limiting sense.

What is claimed is:

1. A method of treating an inflammatory disorder in a mammal which comprises administering to said mammal an effective amount of a compound selected from the group consisting of 3-(N,N-diethylaminoethylamino)-s-triazolo-[3,4-a]-isoquinoline, 3-trifluoromethyl-6-carbomethoxy-s-triazolo-[3,4-a]-isoquinoline, 3-isobutyl-s-triazolo-[3,4-a]-isoquinoline, 8,9-methylenedioxy-s-triazolo-[3,4-a]-isoquinoline, 3-trifluoromethyl-6-methyl-s-triazolo-[3,4-a]-isoquinoline, 3-trifluoromethyl-8,9-methylenedioxy-s-triazolo-[3,4-a]-isoquinoline, 3-trifluoromethyl-9-methoxy-s-triazolo-[3,4-a]-isoquinoline, 3-methyl-9-methoxy-s-triazolo-[3,4-a]-isoquinoline, 3-methyl-8-methoxy-s-triazolo-[3,4-a]-isoquinoline, 3-trifluoromethyl-9-chloro-s-triazolo-[3,4-a]-isoquinoline, 3-trifluoromethyl-8-methoxy-s-triazolo-[3,4-a]-isoquinoline, 3-trifluoromethyl-6-carboxy-s-triazolo-[3,4-a]-isoquinoline, 3-trifluoromethyl-9-methyl-s-triazolo-[3,4-a]-isoquinoline, 3-methyl-7-cyano-s-triazolo-[3,4-a]-isoquinoline, 3-acetoxymethyl-s-triazolo-[3,4-a]-isoquinoline, 3-n-propyl-7-bromo-s-triazolo-[3,4-a]-isoquinoline, 3-methyl-7-chloro-s-triazolo-[3,4-a]-isoquinoline, 3-trifluoromethyl-5,6-dihydro-9-methoxy-s-triazolo-[3,4-a]-isoquinoline, 5,6-dihydro-8,9-methylenedioxy-s-triazolo-[3,4-a]-isoquinoline and the pharmaceutically acceptable, nontoxic acid addition and alkali metal salt thereof.

2. A method as set forth in claim 1 wherein the compound is 3-trifluoromethyl-5,6-dihydro-9-methoxy-s-triazolo-[3,4-a]-isoquinoline.

3. A method as set forth in claim 1 wherein the compound is 3-trifluoromethyl-9-methoxy-s-triazolo-[3,4-a]-isoquinoline.

4. A method as set forth in claim 1 wherein the compound is 3-trifluoromethyl-8,9-methylenedioxy-s-triazolo-[3,4-a]-isoquinoline.

5. A method as set forth in claim 1 wherein the compound is 8,9-methylenedioxy-s-triazolo-[3,4-a]-isoquinoline.

* * * * *